(12) United States Patent
Reicher

(10) Patent No.: US 9,075,899 B1
(45) Date of Patent: Jul. 7, 2015

(54) AUTOMATED DISPLAY SETTINGS FOR CATEGORIES OF ITEMS

(75) Inventor: Murray A. Reicher, Rancho Santa Fe, CA (US)

(73) Assignee: D.R. Systems, Inc., San Diego, CA (US)

( * ) Notice: Subject to any disclaimer, the term of this patent is extended or adjusted under 35 U.S.C. 154(b) by 282 days.

(21) Appl. No.: 13/572,547

(22) Filed: Aug. 10, 2012

Related U.S. Application Data

(60) Provisional application No. 61/522,633, filed on Aug. 11, 2011.

(51) Int. Cl.
G06K 9/00 (2006.01)
G09G 5/00 (2006.01)
G06F 19/00 (2011.01)

(52) U.S. Cl.
CPC .................................. *G06F 19/321* (2013.01)

(58) Field of Classification Search
None
See application file for complete search history.

(56) References Cited

U.S. PATENT DOCUMENTS

| | | | |
|---|---|---|---|
| 6,734,880 B2* | 5/2004 | Chang et al. .................. | 715/738 |
| 2007/0106633 A1* | 5/2007 | Reiner .............................. | 707/1 |
| 2007/0159962 A1 | 7/2007 | Mathavu et al. | |
| 2008/0016111 A1* | 1/2008 | Keen ......................... | 707/104.1 |
| 2008/0126982 A1* | 5/2008 | Sadikali et al. ................ | 715/810 |
| 2008/0136838 A1* | 6/2008 | Goede et al. .................. | 345/619 |
| 2008/0275913 A1 | 11/2008 | van Arragon et al. | |
| 2008/0279439 A1 | 11/2008 | Minyard et al. | |
| 2009/0182577 A1* | 7/2009 | Squilla et al. ...................... | 705/2 |
| 2009/0213034 A1* | 8/2009 | Wu et al. ......................... | 345/1.1 |
| 2009/0248442 A1 | 10/2009 | Pacheco et al. | |
| 2009/0268986 A1 | 10/2009 | Holstein et al. | |
| 2010/0138239 A1* | 6/2010 | Reicher et al. .................... | 705/3 |
| 2010/0211409 A1 | 8/2010 | Kotula et al. | |
| 2010/0246981 A1 | 9/2010 | Hu et al. | |
| 2012/0130730 A1 | 5/2012 | Raizada et al. | |

OTHER PUBLICATIONS

Tahmoush, D. and Samet, H., A New Database for Medical Images and Information, 2007, Medical Imaging 2007: PACS and Imaging Informatics, vol. 6516, pp. 1-9.*
Ivetic, D., and Dragan, D., Medical Image on the Go!, 2009, J Med Syst, vol. 35, pp. 499-516.*
Notice of Allowance dated Mar. 19, 2015 in U.S. Appl. No. 13/572,397.
Office Action dated Jun. 27, 2014 in U.S. Appl. No. 13/572,397.
Final Office Action dated Jan. 13, 2015 in U.S. Appl. No. 13/572,397.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2105 in U.S. Appl. No. 13/572,552.
AGFA HealthCare, color brochure "IMPAX 6: Digital Image and Information Management," ©2012 Agfa HealthCare N.V. Downloaded from http://www.agfahealthcare.com/global/en/he/library/libraryopen?ID=32882925. Accessed on Feb. 9, 2015.

(Continued)

*Primary Examiner* — Stephen R Koziol
*Assistant Examiner* — Jonathan S Lee
(74) *Attorney, Agent, or Firm* — Knobbe, Martens, Olson & Bear LLP

(57) ABSTRACT

Provided herein are various systems and methods for customizing display of items associated with medical exams based on one or more categories (for example) associated with respective items.

18 Claims, 9 Drawing Sheets

(56) References Cited

OTHER PUBLICATIONS

AGFA HealthCare, IMPAX 6.5 Datasheet (US)2012. ©2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR5032Rev.°/0204interWORKS%2ORISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV0001 REVC). Downloaded from http://www.brit.com/pdfs/BPB-BVV0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 19972009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 (Jun.), 2007; pp. 105-113.
Erickson, et al.: "Image Registration Improves Confidence and Accuracy of Image Interpretation," Special Issue-Imaging Informatics, Cancer Informatics 2007: 1 19-24.
FUJIFILM Medical Systems, SYNAPSE@ Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 p. color brochure, (XBUSSY082) Aug., 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_inform atics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
imageanalysis, dynamika, 2 page color brochure. Downloaded from http://www.imageanalysis.org.uk/what-we-do. Accessed on Feb. 9, 2015.
imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
lnfinitt, PACS, RIS, Mammo PACS, Cardiology Suite and 3D/Advanced Visualization I lnfinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wpcontent/uploads/sites/Feb. 2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014

(56) References Cited

OTHER PUBLICATIONS

Medweb. Downloaded from http://www.medweb.com/docs/rispacs_brochure_2014.pdf. Accessed on Feb. 9, 2015.

Mendelson, et al., "Informatics in Radiology—Image Exchange: IHE and the Evolution of Image Sharing," RadioGraphics, Nov.-Dec. 2008, vol. 28, No. 7.

Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.

NOVARAD Enterprise Imaging Solutions, NOVAPACS, 2 page (color) printout. Accessed at http://ww1.novarad.net/novapacs. Accessed on Feb. 9, 2015.

PACSPLUS, PACSPLUS Server, 1 page (color) printout. Accessed at http://www.pacsplus.com/01_products/products_01.html. Accessed on Feb. 9, 2015.

PACSPLUS, PACSPLUS Workstation, 3 p. (color) printout. Accessed at http://www.pacsplus.com/01_products/products_01.html. Accessed on Feb. 9, 2015.

PHILIPS IntelliSpace PACS, in 2 color page printout. Accessed at https://www.healthcare.philips.com/main/products/healthcare_informatics/products/enterprise _imaging_informatics/isite_pacs. Accessed on Feb. 9, 2015.

RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.

Sage Intergy PACS | Product Summary. Enhancing Your Workflow by Delivering Web-based Diagnostic Images When and Where You Need Them, in 2 color pages. (IRV-SSINTPACS-PSS-031309). © 2009 Sage Software Healcare, Inc. Downloaded from http://www.greenwayhealth.com/solutions/intergy/. Accessed on Feb. 9, 2015.

Schellingerhout, Dawid, MD, et al.: "Coregistration of Head CT Comparison Studies: Assessment of Clinical Utility," Acad Radiol 2003; 10:242-248.

ScImage, Cardiology PACS, in 8 color page printout. Accessed at http://www.scimage.com/solutions/clinical-solutions/cardiology. Accessed on Feb. 9 2015.

Sectra RIS PACS, in 2 color page printout. Accessed at https://www.sectra.com/medical/diagnostic_imaging/solutions/ris-pacs/. Accessed on Feb. 9, 2015.

Siemens syngo.plaza, Features and Benefits, in 2 color page printout. Accessed at http://www.healthcare.siemens.com/medical-imaging-it/imaging-it-radiology-imagemanagement-pacs/syngoplaza/features. Accessed on Feb. 9, 2015.

Simms | RIS and PACS Medical Imaging Software, in 2 color page printout. http://www.mysimms.com/ris-pacs.php. Accessed on Feb. 9, 2015.

Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.

Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.

UltraRAD—ultra VISION, 1 page (color). Downloaded from http://www.ultraradcorp.com/pdf/UltraVISION.pdf. Accessed on Feb. 9, 2015.

VioStream for VitreaView, 2 color pages printout. Accessed at http://www.vitalimages.com/solutions/universal-viewing/viostream-for-vitreaview. Accessed on Feb. 9, 2015.

Visage Imaging Visage 7, 3 color page printout. Accessed at http://www.visageimaging.com/visage-7. Accessed on Feb. 9, 2015.

VIZTEK Radiology PACS Software Vixtek Opal-RAD, 4 color page printout. Accessed at http://viztek.net/products/opal-rad. Accessed on Feb. 9, 2015.

Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.

Voyager Imaging—Voyager PACS, 3 page color brochure. Downloaded from http://www.intellirad.com.au/index.php/assets/Uploads/Voyager-Pacs3.pdf. Accessed on Feb. 9, 2015.

Tahmoush, D. and Samet, H., A New Database for Medical Images and Information, 2007, Medical Imaging 2007; PACS and Imaging Informatics, vol. 6516. Pages 1-9.

* cited by examiner

FIG. 4

External Exam Description

External Exam Description
- exam Description: HEAD CT WO
- Modality: CT
- Active Status: Active

Link Exam Type
- Exam Code: 57501
- Modality: CT
- Exam Description: HEAD WO
- Procedure: CT OF THE HEAD
- Active Status: ACTIVE
- DICOM Modality: CT Link...

OK  Cancel

AUTOMATED DISPLAY SETTINGS FOR CATEGORIES OF ITEMS

CROSS-REFERENCE TO RELATED APPLICATIONS

This application claims the benefit of priority under 35 U.S.C. §119(e) of U.S. Provisional Application No. 61/522,633, filed Aug. 11, 2011, the disclosure of which is hereby incorporated by reference in its entirety.

BACKGROUND

There is a need for innovations that increase the efficiency and accuracy of interpretation of medical imaging exams.

SUMMARY

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In one embodiment, a method of customizing display of objects comprises monitoring selection of items for display on one or more display devices of a computing system, wherein the items include one or more documents, images, forms, and/or dialogs associated with a patient, monitoring changes in one or more of a size or position of items displayed on the one or more display devices, and, in response to detecting a change in one or more of a size or position of a particular item of the items displayed on the computing device, creating or updating item information associated with the item. In one embodiment, the item information includes a category associated with the item, a user of the computing system, one or more display characteristics of the one or more display devices on which the particular item is displayed, associations between a size and/or position of the particular item after the detected change, the category, the user, and the one or more display characteristics, wherein the associations are usable by the computing system and/or other computer systems in order to automatically adjust a size and/or position of other items selected for display that are also within the category, such that a size and position of the other items match the size and position of the particular item.

In one embodiment, the item information is further associated with a medical exam such that subsequent selection of the medical exam results in display of the particular item at the size and position stored in the item information. In one embodiment, the item information further comprises associations between one or more other items and respective sizes and/or positions, categories, users, and display characteristics.

In one embodiment, the item information further comprises an arrangement of multiple items of an exam such that subsequent selection of the exam results in display of the multiple items at the respective sizes and positions stored in the associations information. In one embodiment, the item information is stored with and/or associated with the exam. In one embodiment, the item information is stored on a network accessible device so that the item information is accessible to determine the arrangement and/or size and position of items of the exam selected on other computing systems. In one embodiment, the categories comprise documents, images, forms, and/or dialogs. In one embodiment, the categories comprise types of documents, types of images, types of forms, and/or types of dialogs. In one embodiment, the one or more display characteristics include one or more of a resolution of the one or more displays, an aspect ratio of the one or more displays, and whether the one or more displays are color or black and white.

In one embodiment, the item information further comprises associations between a second size and/or position, the same determined category, the same determined user, and a second one or more display characteristics. In one embodiment, the method further comprises, in response to selection of a second particular item for display on a display device having about the second one or more display characteristics, adjusting a size and/or position of second particular item to the size and position associated with the second one or more characteristics. In one embodiment, the display device is determined to have about the second one or more display characteristics if a resolution of the display device is less than 5% different than a resolution included in the second one or more display characteristics.

In one embodiment, the method further comprises providing a user interface on a first of the one or more display devices for selection of the particular item for display on a second of the one or more display devices having the determined one or more display characteristics such that the particular item is selected by the user interface on the first of the one or more display devices and displayed on the second of the one or more display devices.

In one embodiment, the method further comprises determining whether a second display device is within a range of acceptable characteristics for displaying the particular item according to the item information, and in response to user selection of the particular item for display on the second display device, only use the size and/or position of the particular item if the second display device is within the range of acceptable characteristics.

In one embodiment, the item information further comprises information indicating an arrangement of multiple categories of items displayed on the one or more display devices. In one embodiment, the method further comprises, in response to selection of a plurality of items for display, determining whether the multiple categories of items are included in the plurality of items and, in response to determining that the multiple categories of items are included in the plurality of items, determining a size and/or position of the plurality of items according to the item information associated with the respective categories. In one embodiment, the item information indicates respective display devices on which items of respective categories are displayed.

In one embodiment, the computing system and/or other computer systems automatically adjust a size and/or position of other items selected for display that are also within the determined category in response to determining that a resolution of the computing system and/or other computer system is about the determined resolution.

BRIEF DESCRIPTION OF THE DRAWINGS

FIG. 4 is another sample screen shot of information displayed on a monitor including, in this specific example, an Advanced Beneficiary Notice and a clinical report template.

FIG. 6 is a sample user interface that may be displayed to a user when a non-matching exam type is ordered, received, or otherwise accessed.

FIG. 7 illustrates a sample screenshot of a user interface that may be used to link a form with one or more of an exam type, insurance plan, acquisition site, or other link.

FIG. 8 illustrates a sample screenshot of a user interface that allows selection and/or viewing of an attribute indicating whether or not a particular form needs to be returned to the medical facility (e.g., after completion by a patient).

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. In other embodiments, users may include any individuals or groups of individuals that generate, transmit, view, and/or otherwise work with images of any type. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Montage Customizations

Figure 1:
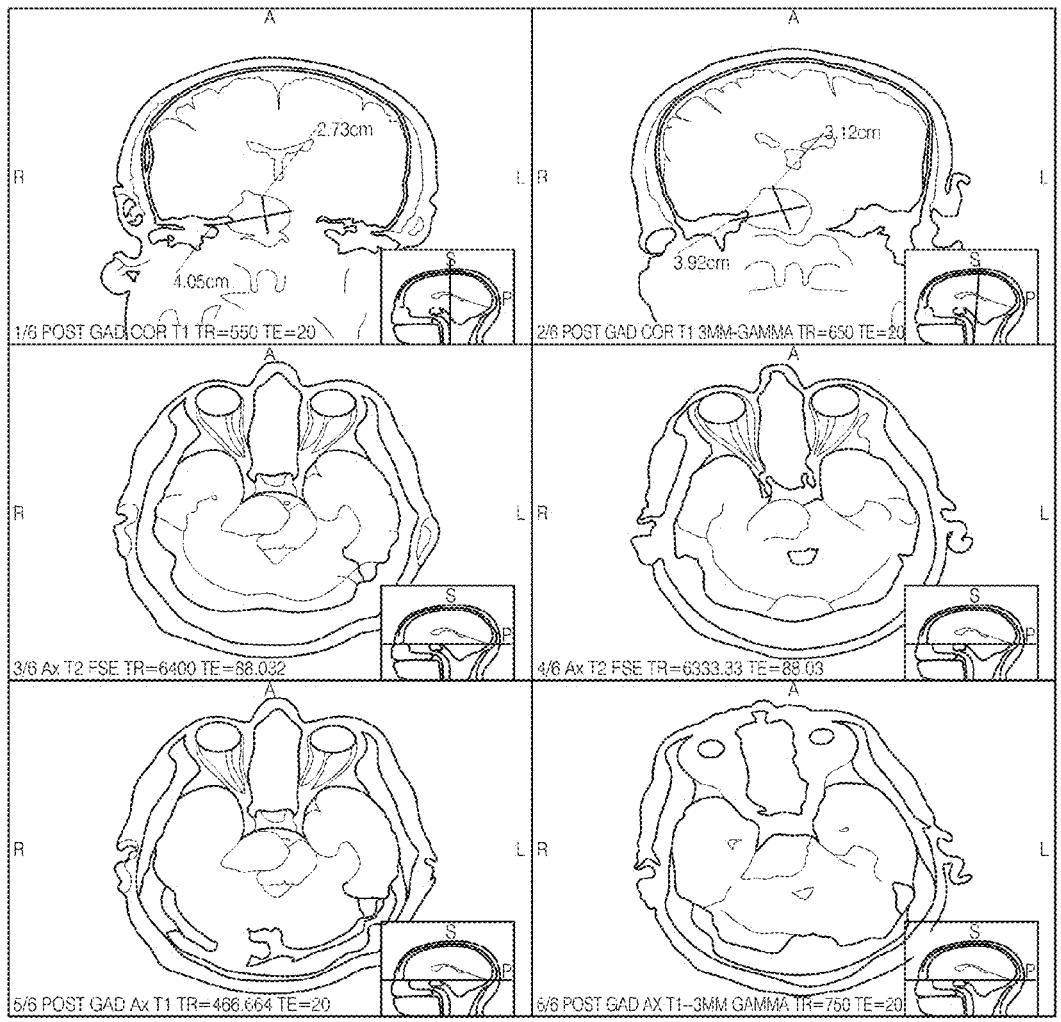
FIG. 1 is a sample montage that may be displayed on a computing device of a user, such as a radiologist or doctor.
Figure 2:
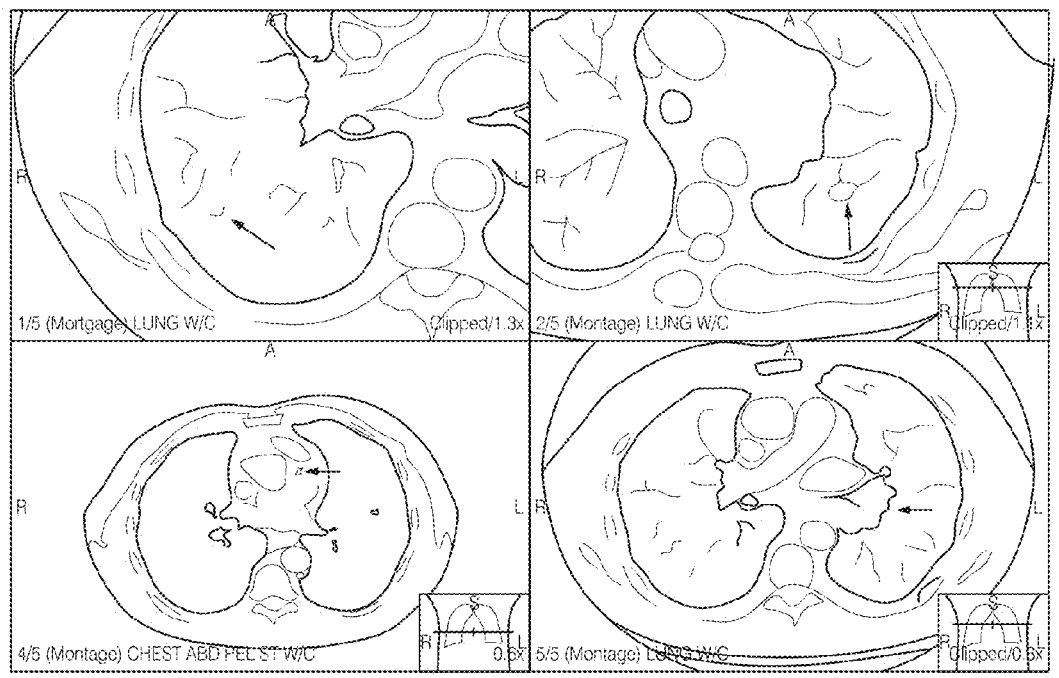
FIG. 2 is another example of a montage with a different number of images, including images that are formatted differently and include annotations (e.g., arrows pointing to areas of specific interest).

FIG. 1 is a sample montage that may be displayed on a computing device of a user, such as a radiologist or doctor. In the illustration of FIG. 1, the images of the montage are those selected by the reading physician as key images, such as at the time of review of an MRI of the Brain. The exam may include several image series, and hundreds or thousands of images. In one embodiment, the radiologist composes the montage by selecting one or more key images from one or more image series, and by adjusting various view settings of the images, such as window/level settings, centering, cropping, magnification, annotations, insets, etc. The same image might be selected more than once, but shown on the montage with different window/level settings, centering, cropping, magnification, annotations, insets, etc. FIG. 2 is another example of a montage with a different number of images, including images that are formatted differently and include annotations (e.g., arrows pointing to areas of specific interest).

In one embodiment, montages are saved as separate files, such as separate image files that are essentially a screenshot of a montage (e.g., a snapshot of the montages of FIG. 1 or 2). Thus, the montage that is configured by the viewer (e.g. radiologist or doctor) may be recalled at a later time. In one embodiment, the montage image file may be notated as a key image, such as according to the DICOM (Digital Imaging and Communications in Medicine) specification. The montage might include images from multiple examinations, or might include reference images such as illustrations or medical images exemplifying pathological or normal conditions.

In another embodiment, a montage having 1 or more images can be stored in one or multiple ways, including (1) storage of the complete composite montage image and/or (2) storage of sufficient information regarding each image so that the entire montage can be recreated upon future display or the individually stored images can be displayed, depending on the user's preferences, depending on the display environment (such as aspect ratio of the display window, monitor resolution, a combination of user preferences and display environment, or other factors.) For example, information regarding the arrangement of images in the montage, as well as information regarding display settings of respective images (e.g., magnification, brightness, centering, cropping, filters, annotations, insets, etc.) may be stored. These montage characteristics may then be recalled at a future time and used to re-build the montage. In this embodiment, storage of an image of the entire montage may not be necessary, while in other embodiments the montage image (e.g., a snapshot of the montage) may be stored and used in certain circumstances, such as when the montage is to be displayed on a display having essentially the same resolution and aspect ratio as the display on which the montage was originally created. As used herein, the arrangement information included in montage characteristics may include a number of rows and columns of medical images in the montage, indications of specific locations of each medical image in the montage, indications of an order that medical images of the montage are displayed, and/or any other information that may be usable to read construct a montage on the same or another computing device based on the layout of the montage images.

Additionally, other information related to the montage display/configuration may be stored (and later accessed to rebuild the montage or a montage of different images in the same configuration). For example, information regarding the device on which the montage was generated may be stored. In one embodiment, the resolution of the display device and/or size of a window in which the montage is created (e.g., horizontal pixels by vertical pixels) may be stored. Thus, the system (e.g., the device that will display the images and/or a device that is serving the images) may automatically select the format of the montage (such as 4×2 vs. 2×4) based on the aspect ratio of the images compared to the aspect ratio/orientation of the monitor. In another embodiment, the montage may be displayed in a manually sizable window, and the format of the montage may be automatically and optionally dynamically adjusted based on the aspect ratio of the window. In another embodiment, as images are added to the montage, the display format is automatically adjusted based on the aspect ratio of the montage window, the aspect ratio of the added images, and/or the number of images added.

Similarly, orientation of the display device (e.g., portrait or landscape), as well as matrix information (e.g., the number of rows and columns of images, e.g., 4 images×2 images or 6 images×4 images) may be stored in a set of montage characteristics (e.g., a file that is associated with an exam or added to header information to one or more exam files). Thus, multiple sets of montage characteristics that include the same (or some of the same) images may be stored and selected based on characteristics of the computing device that later displays the montage, such as the display size. Accordingly, a first set of montage characteristics may be automatically selected for viewing of images of a particular exam on a tablet computer while a second set of montage characteristics may be automatically selected for viewing of images of the same particular exam on a desktop computer with a monitor having a much higher resolution. The computing device that displays the montage may automatically select the appropriate set of montage characteristics, without any input from the user. For example, montage characteristics may be stored with a particular exam, such that when that exam is later recalled by any computing system, montage characteristics may be accessed in order to reconstruct part or all of the montage. In some embodiments, montage characteristics are used by a viewing computing system to rebuild all (or parts of the montage) according to rules for doing so, such as user or system rules. Thus, the montage characteristics essentially provide information that is usable by a viewing computing system to view portions or all of the montage in accordance with a viewing environment and/or user preferences.

In one embodiment, the multiple images of a montage are simultaneously saved as key images (e.g., key DICOM objects) so that the images may be easily identified for inclusion in a montage that is generated based on stored montage characteristics.

As noted above, montage characteristics may be automatically selected based on the user, the display monitor (such as its resolution, aspect ratio, Smartphone vs PC monitor, etc), and/or other characteristics of an image viewing environment. Montage characteristics may be used to display the entire montage in the arrangement originally used by the viewer. In one embodiment, the user may cycle through other images of images series to which key images belong, keeping the same display characteristics as the key image as a default.

In another embodiment, an image may be one of many images in an image series, such as one axial image of a number of stacked axial images of the patient. In this case, in one embodiment, when an image is added to the montage the system may retain information related to the entire series of images so that a user may manipulate the montage image to also access other images in the same series.

By saving the key object information, a user can preserve the ability to manipulate each image individually, even when the images are displayed in the grouped montage mode.

Customized Display of Documents/Dialogs

Figure 3:
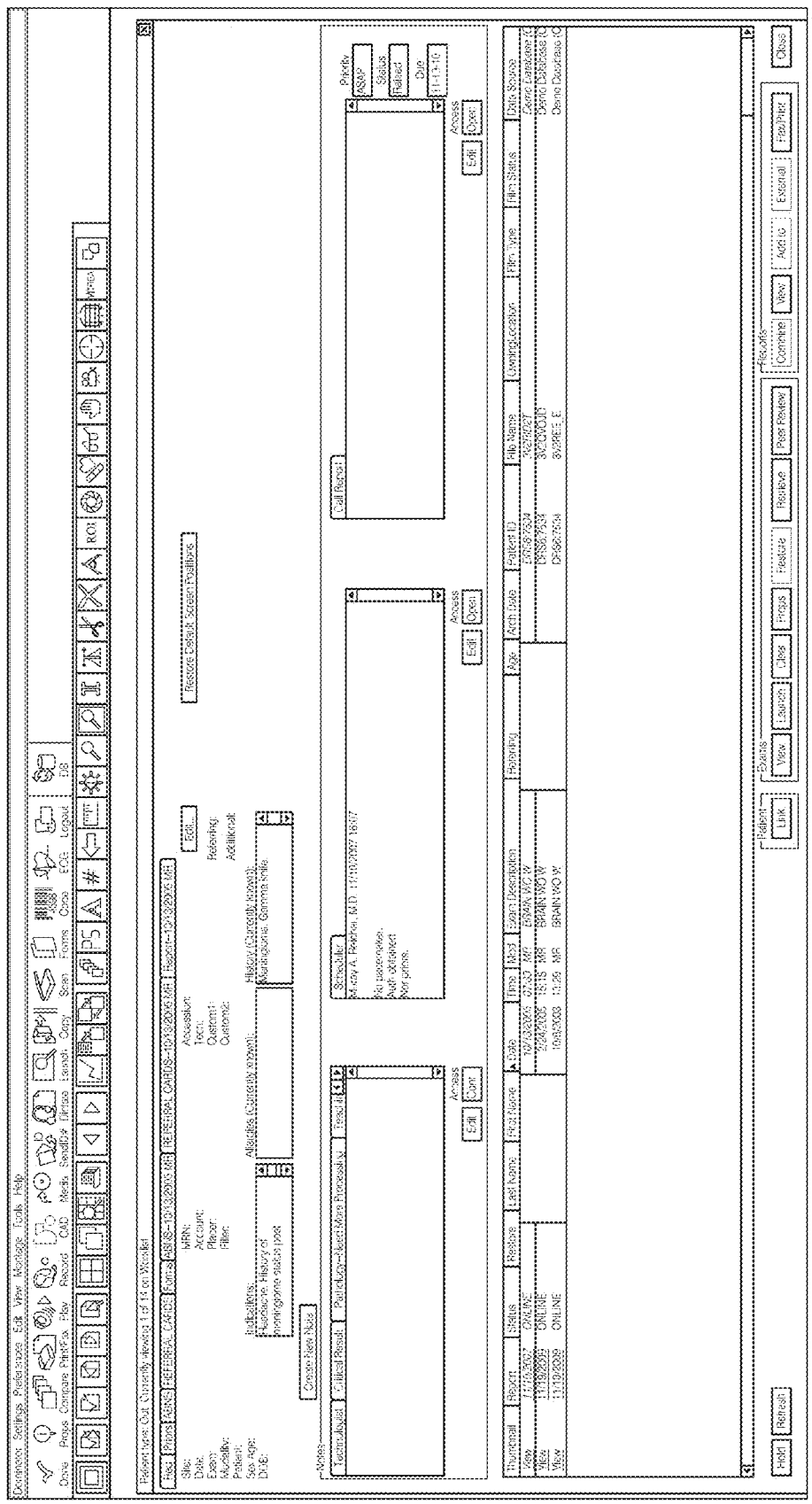
FIG. 3 is a sample screen shot of information displayed on a monitor by image viewing/manipulation software, such as DR Systems Unity RIS/PACS.
Figure 4:
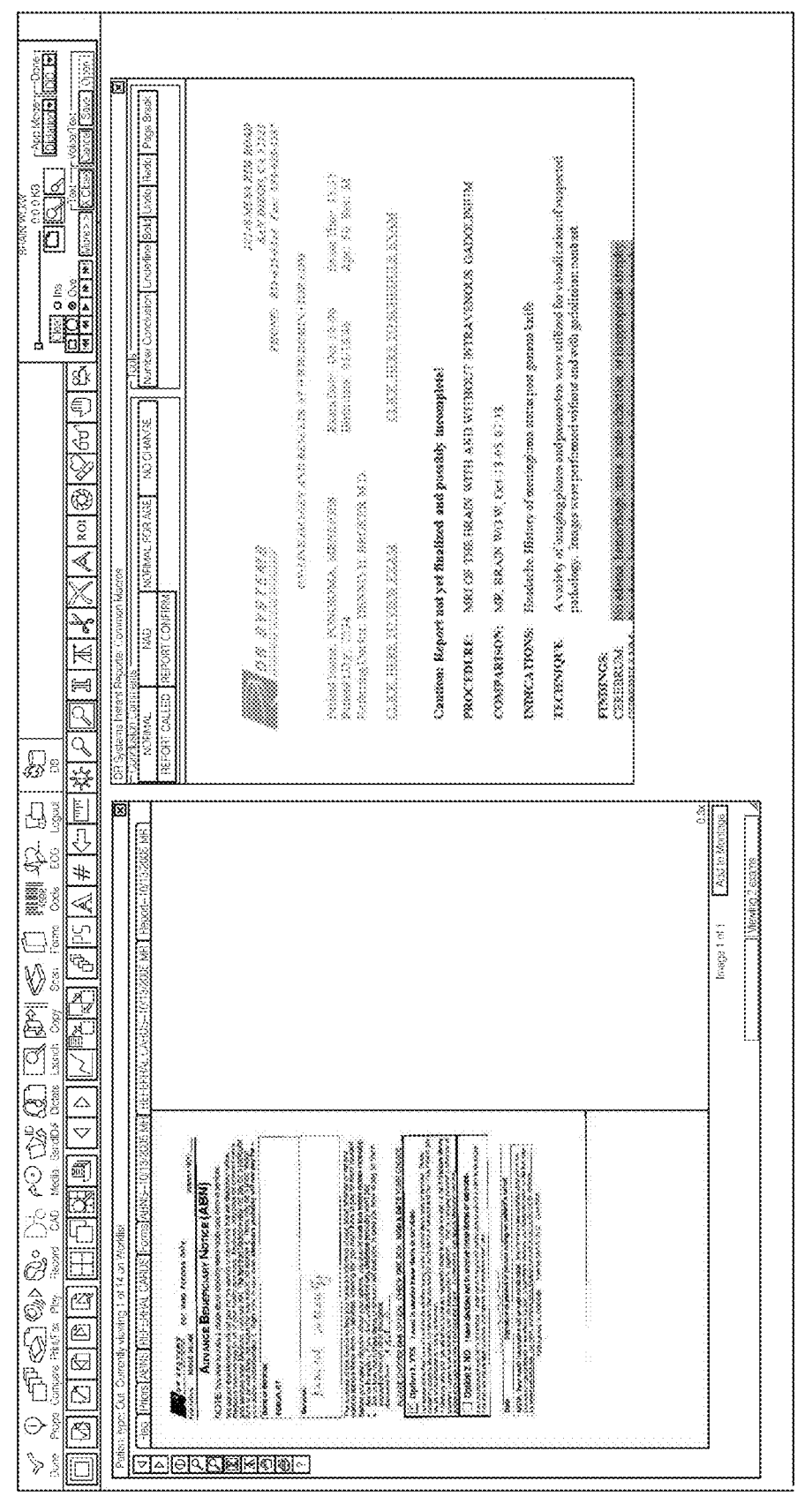

FIG. 3 is a sample screen shot of information displayed on a monitor by image viewing/manipulation software, such as DR Systems Unity RIS/PACS. The large dialog that fills most of the screen may be referred to as the Requisition, and it contains several tabs, some shown in red (the last three tabs) and others in blue (the first five tabs). Each tab represents a document or dialog associated with one or more imaging exams that are currently displayed on other monitors of a multi-monitor system. For example, FIG. 4 is a sample screen shot of one such arrangement, where the clinical report template associated with the current exam is displayed on the right, and a scanned document (Advanced Beneficiary Notice) is shown on the left.

In some scenarios, a reading physician may want to display the Requisition and the various available documents/dialogs/webforms according to a preferred layout (e.g., a user-preferred layout), including size and position of various available elements. For example, with reference to FIG. 4, the user may have displayed the Advanced Beneficiary Notice by selecting one of the tabs from the upper left of the requisition, via another mouse action, keyboard shortcut or audio command, and also displayed the clinical report template through another means, such as a button click, mouse click, hotkey, or audio command. After selecting documents/dialogs for display, the user can adjust the size and position of these objects. Repeating these actions for other patients/exams is repetitive and not efficient. There can be many tabs available on the requisition or elsewhere for display of various categories of display objects, such as clinical reports, scanned documents, photographs, forms, prior exam lists etc.

In one advantageous embodiment, when a user sizes and positions a window, the system remembers that size and position for that category of item (e.g., any object) and for the user (or user group), such as by storing an association between the size and position of the item with the determined category in "item information." The system may then automatically recreate that sizing and layout in the future for that user when a document of the category is displayed, suing the item information. Accordingly, each user can size and position these various documents/dialogs, and the system will remember the layout for any workstation across the network that uses a monitor of the same matrix size, while defaulting to a standard configuration for monitors of a different matrix size. In one embodiment, a single user may have multiple arrangements of documents/dialogs that are associated with different monitor sizes that are used by the user. In some embodiment, display settings may be stored for specific documents/dialogs as well, or as an alternative to the category settings discussed above.

In one embodiment, the display characteristics are associated with a display size (e.g., the matrix size and/or orientation of a monitor on which the document/dialog was viewed), such that the sizing and layout of documents of that category are displayed in that manner only when requested for viewing on the same or similar display configuration. In this embodiment, the system may select a default display layout for other monitor formats. If the user then sets the sizing and layout for another monitor format, the system will remember both set-ups for the user and make those layouts available to other devices throughout a network, such as a WAN or LAN. Any number of set-ups can be remembered.

Figure 5:
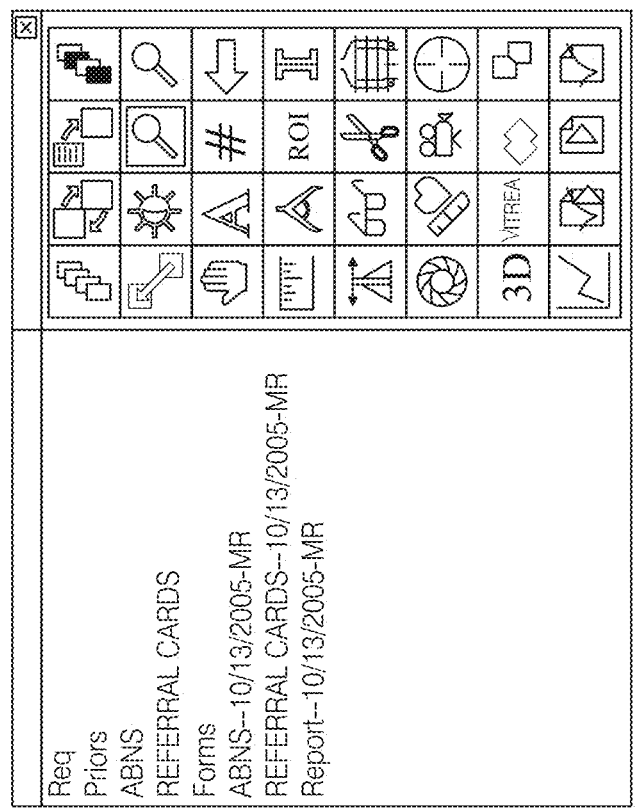
FIG. 5 illustrates a sample toolbox that may be used to select items for display on multiple monitors.

In one embodiment, the user can open a toolbox, such as the sample toolbox of FIG. 5, from any of multiple monitors by clicking a keyboard shortcut or mouse button, or via an audio command. This toolbox includes a list of all of the display objects available on the Requisition or other objects. The user can select any item on the list to immediately display the desired object, and the object will appear in the location associated with the item information for a category of the object based on the users stored display layout preference or the default layout preference. Thus, the user does not need to drag a mouse to the monitor on which he wants to display the object, and one can control the display of an object on one monitor or in one display window, while working from another monitor or another display window. For example, a single monitor may be large enough to display many windows that might have previously required many monitors. In such an embodiment, the systems and methods discussed herein allow automatic positioning on the single monitor at a location associated with the user account. A reading physician who is viewing images on another monitor (or in another window of a same monitor) can thus control the display of objects on a first monitor without first dragging a mouse or distracting his vision to the first monitor. When the object appears, it follows the stored set-up instructions.

Exam Description Mapping

RIS, PACS, and other healthcare information systems typically contain a table of Exam Types, which is a list of various medical imaging exams available for selection. The Exam Type table (or "Exam type master file") may include exam descriptions, modality descriptions, alphanumeric codes, as well as other information about each Exam Type—such as the default title of a clinical report based on that Exam Type, forms that should appear to the user (clerk, patient, technologist, and/or doctor) when that Exam Type is performed or viewed, linked clinical report templates, linked information about required supplies, clinical protocols, payment policies, charges, relative value/productivity units, safety policies and more. In addition, various user or site preferences can be based on the Exam Type or modality, such as which exams should be automatically restored from archive for comparison when a particular Exam Type is scheduled or performed, which and how many exams are displayed for comparison when an exam is viewed, how a particular user prefers images to be displayed, and more. In addition, system automation may depend on the Exam Type table, such as rules automating the pre-fetching of prior comparison exams, reading physician protocols for exam display, automated creation of virtual series, keyboard shortcuts, reading sequences, routing of exams, and more. Therefore, in a sense, the Exam Type master file is a sort of DNA of some healthcare information system.

When a RIS/PACS or other related information system receives medical images or orders from external system, the Exam Type information may or may not match up with information already present in the Exam Type table. For example, exams of the same type may be named differently by different acquisition/viewing system. This information might be exchanged via information in a DR RIS, CVIS, DICOM metafile, in an HL-7 message, an order message, billing message, etc. In one embodiment, the system may offer configuration options that specify how the system should respond to a non-matching Exam Type, such as by either holding the processing of the message or exam import, or automatically adding the non-matching Exam Type to the Exam Type master file. However, either of these options prevents automated performance of actions that are customized for a particular exam type due to a non-matching Exam Type. In fact, setting up actions for a non-matching Exam Type often requires manual intervention. Alternatively, automatically adding a non-matching Exam Type to the Exam Type master file may disrupt automated steps that are dependent on a precisely linked and set-up list of Exam Types.

In order to make more efficient use of the Exam Type master file, in one embodiment an Exam Type mapping function is defined so that when a non-matching Exam Type is encountered by the system via the variety of different possible messages described above, the system prompts the user (in one or more of many possible manners—such as either a pop-up message, generation of a worklist, text-message of other means) that a non-matching Exam Type was encountered. The user can then map the non-matching Exam Type to the proper Exam Type from the master file, so that if the non-matching Exam Type is again encountered, it can be automatically processed (e.g., without any notification to the user). As a result, and depending on the type of in-bound message, the system might create a new scheduled exam with the internally mapped Exam Type, or import a DICOM imaging exam with the proper internally mapped Exam Type. All of the system automation that depends on the internally mapped Exam Type may then properly occur.

FIG. 6 is a sample user interface that may be displayed to a user when a non-matching Exam Type is ordered or received. In this embodiment, the Exam Description may be mapped to an Exam Type already stored in the Exam Type master file so that future exams having the same Exam Description are automatically mapped to the selected Exam Type and its corresponding actions.

In one embodiment, in addition to providing the ability to manually map Exam Types as discussed above, the system could apply rules that map Exam Types based on relative matching of character strings or other best match rules related to Exam Codes or other message characteristics. Based on a confidence level of a match, the automated mapping may be applied without further input from the user. For example, if a confidence level of a match is lower (e.g., below 80%) the user may be provided with the most likely matches and provided an opportunity to select from the short list of possible matches, rather than navigating through a list of all Exam Types in the master file.

In one embodiment, this mapping may be applied not only to inbound messages/exams, but also to outbound messages returning to external information systems, so that any edits, changes, and/or updates could be communicated back to the original system.

Automated Forms to Patient Portal

Patient forms may be created and stored as form templates that are referred to in a data structure that links respective form templates with various links. The links can indicate when the forms are automatically presented and where they are automatically filed. For example, a particular form might be linked to a particular insurance, patient sex, patient language, age group, exam type, modality, or other stored information. As a result, when a scheduled exam is selected, the proper forms for that patient can be automatically presented for printing or electronic completion. In addition, the form templates can be linked to a specific naming convention and storage location. For example, one might create a CT Consent Form template and an MRI Consent Form template, and store information such that when either of these templates is used to create a CT Consent Form or MRI Consent Form, these forms are stored with the patient record such that they are labeled as Consent Forms, whereas there might be other form templates that would be stored as Insurance Forms, or Release Forms, etc.

Figure 7:
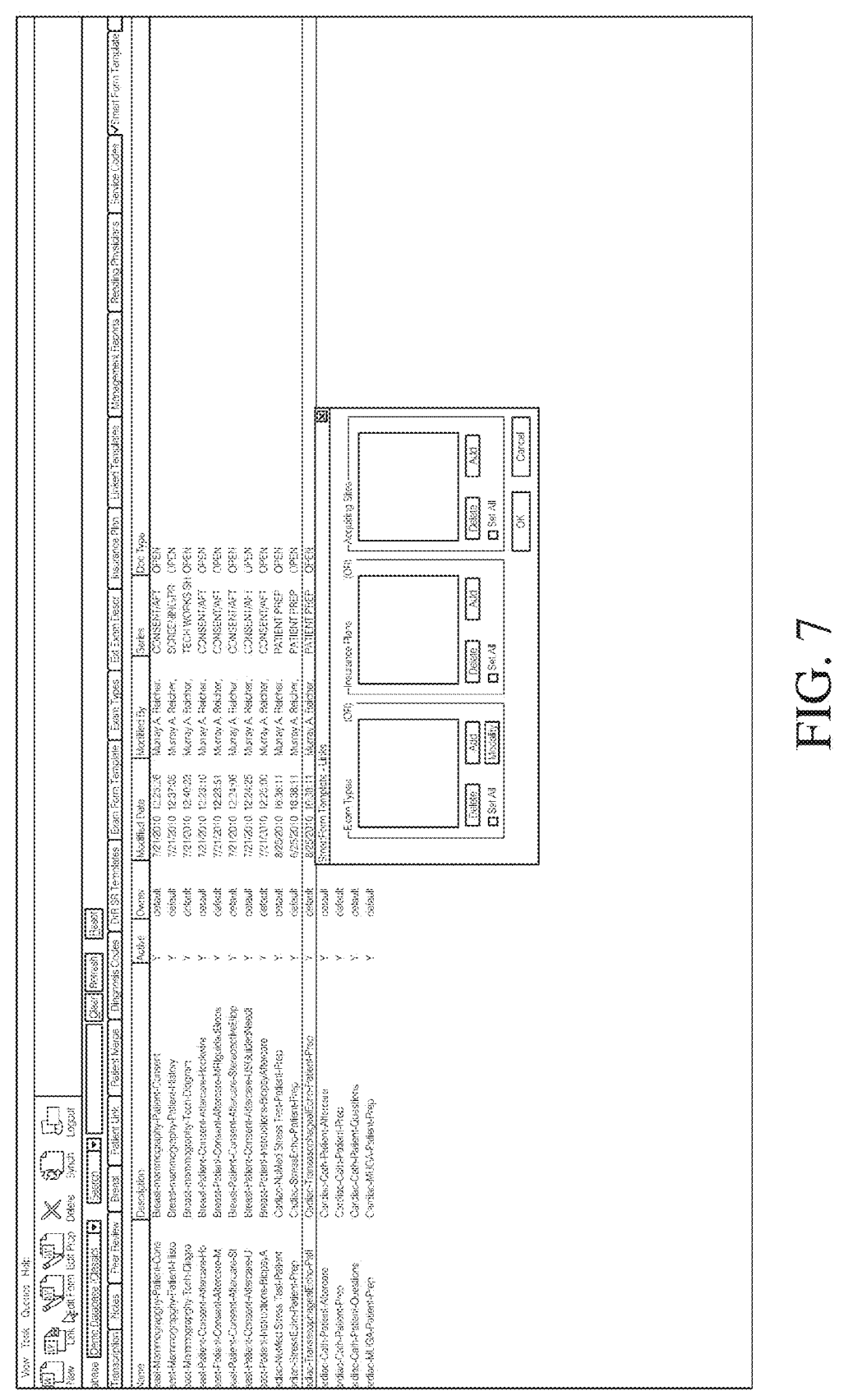

In one embodiment, when an exam is scheduled, the proper forms based on the automated links are posted to an internet-accessible location where the proper patient can view, print, or complete the forms. The forms may be automatically labeled with an indentifying barcode, so that if the patient prints and completes the forms on paper, the paper can later be scanned, the bar code identified, and the form thus automatically filed with the proper patient, proper exam, and proper label. Each instance of a form may be provided with a specific identifier so that the information provided in the form (e.g., electronically or manually) may be associated with the proper patient's record and/or exam, and labeled properly. FIG. 7 illustrates a sample screenshot of a user interface that may be used to link a form with one or more of an Exam Type, Insurance Plan, Acquisition Site, or other link.

Figure 8:
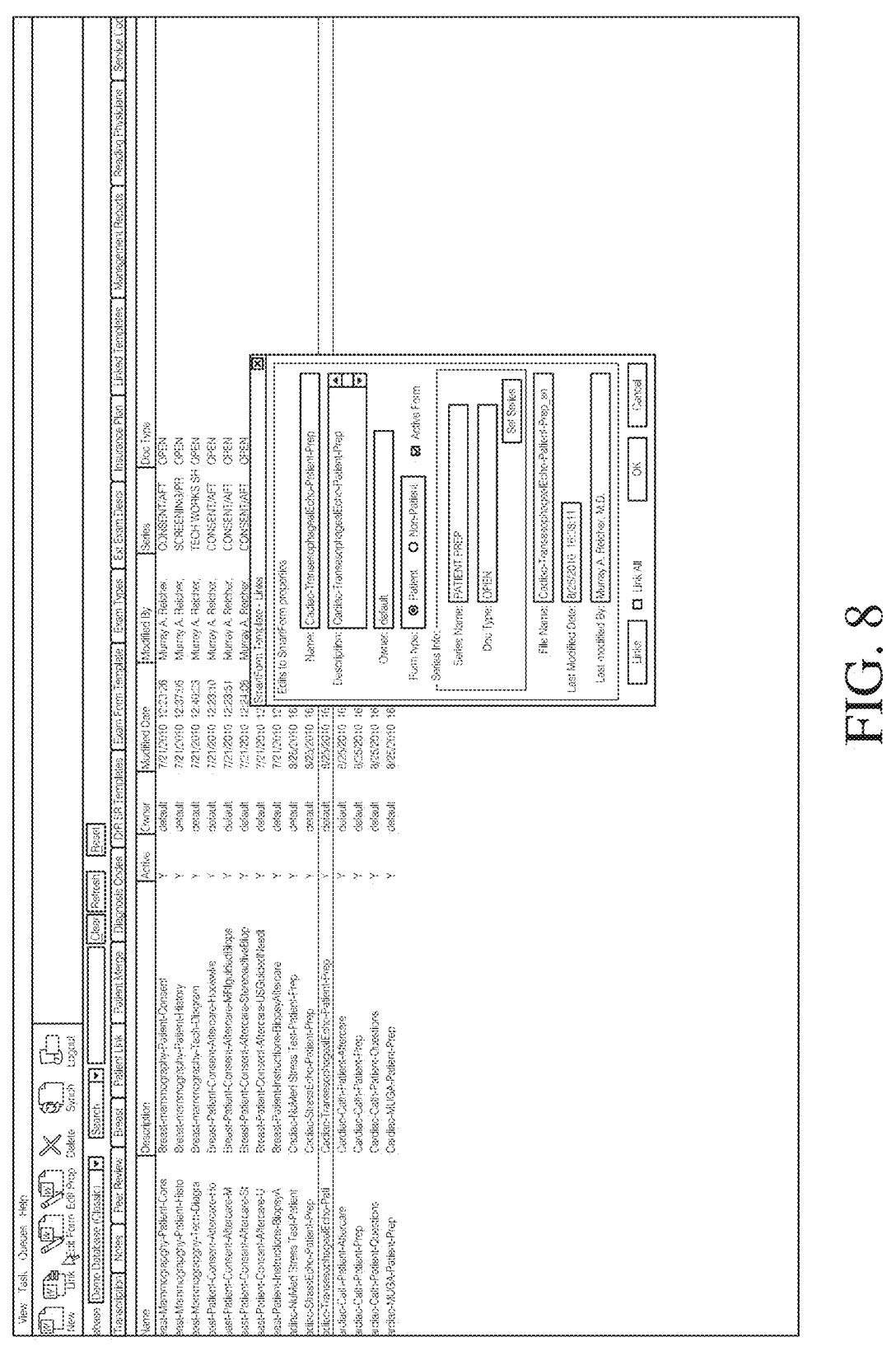

FIG. 8 is a screenshot of a sample user interface that may be accessible by a "Set Series" or similar button. The user interface allows the user to specify the category or series name that will be used to store instances of the form that are created using one of the templates stored in this list. Note that the templates might be one of many types of document formats, including MSWord, HTML, XML, CDA, CCR, etc. By placing a barcode on a printed form or by associating information with an electronic form, the system can automatically store the instance of the form with the proper patient, proper exam, and in the proper series. The series information may also further specify if, how, and when the form is presented for any particular user or by system default.

In one embodiment, forms may be associated with an attribute that indicates whether the form must be returned to system (e.g., to the medical facility that originally provided the form). Depending on various factors (e.g., reasons for visiting a medical facility), some quantity of forms provided to a patient may be for use of the patient (and/or a party other than the medical facility that provides the forms) and, thus, are not required to be returned to the medical facility. For example, a medical facility may not want forms that provide informational content to the patient returned to the medical facility. However, many forms provided to the patient may need to be returned to the medical facility and/or required to be returned prior to performance of an exam or procedure, for example. Thus, an attribute indicating whether or not a particular form needs to be returned to the medical facility may be indicated using a user interface similar to that shown in FIG. 8. A patient's file may then be automatically reviewed in order to determine if any forms that are required to be returned have not yet been returned (possibly a certain number of days after the forms are provided or a certain number of days before a scheduled exam).

Example System Implementation

Figure 9:
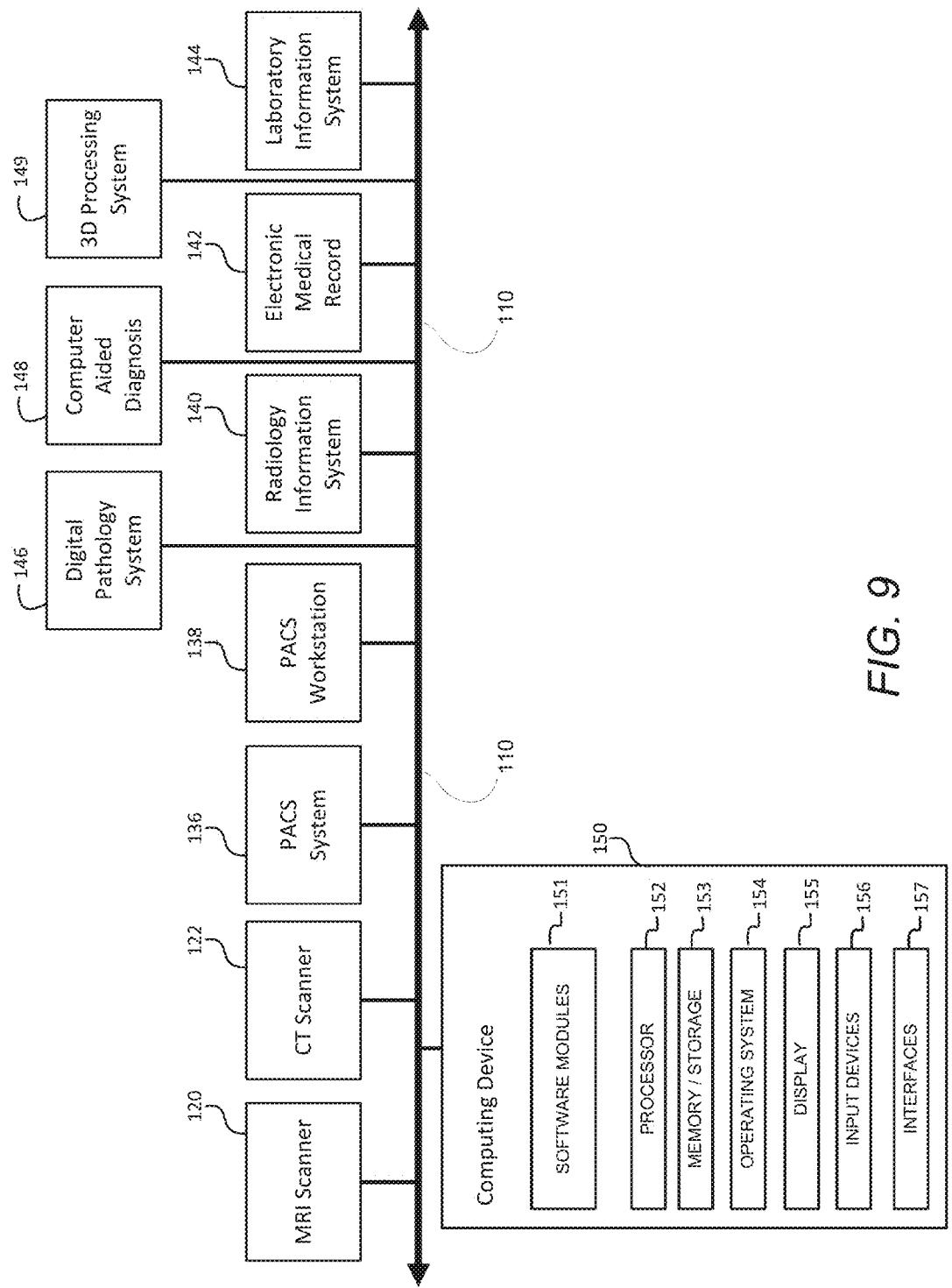
FIG. 9 is a system diagram which shows the various components of a system for performing the system and methods described above.

FIG. 9 is a system diagram which shows the various components of a system 100 for performing the system and methods described above, wherein the configuration of the system 100 may include fewer or additional features than are illustrated and individual components, such as the computing device 150, may also include fewer or additional components. In one embodiment the methods discussed above as being performed by "a system" are performed by the computing device 150. In other embodiments, the methods may be performed by any other suitable computing device.

The Computing Device 150 may take various forms. In one embodiment, the Computing Device 150 may be a computer workstation having software modules 151. In other embodiments, software modules 151 may reside on another computing device, such as a web server, and the user directly interacts with a second computing device that is connected to the web server via a computer network.

In one embodiment, the Computing Device 150 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The Computing Device 150 runs an operating system 154, such as an off-the-shelf operating system, for example, Windows, Linux, MacOS, Android, or iOS operation system. The Computing Device 150 may also run a more specialized operating system which may be designed for the specific tasks performed by the computing device 150.

The Computing Device 150 may include one or more computing processors 152. The computer processors 152 may include central processing units (CPUs), and may further include dedicated processors such as graphics processor chips, or other specialized processors. The processors generally are used to execute computer instructions based on the software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, data structures, data structures, tables, arrays, and variables. For example, modules may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The Computing Device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The Computing Device 150 may also include or be interfaced to one or more display devices 155 that provide information to the users. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The Display Computing Device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The Computing Device 150 may also include one or more interfaces 157 which allow information exchange between Computing Device 150 and other computers and input/output devices using systems such as Ethernet, Wi-Fi, Bluetooth, as well as other wired and wireless data communications techniques.

The modules of Computing Device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of Computing Device 150 may be combined into fewer components and modules or further separated into additional components and modules.

Computing Device 150 may communicate and/or interface with other systems and/or devices. In one or more embodiments, the computing device 150 may be connected to a computer network 110.

The computer network 110 may take various forms. It may be a wired network or a wireless network, or it may be some combination of both. The computer network 110 may be a single computer network, or it may be a combination or collection of different networks and network protocols. For example, the computer network 110 may include one or more local area networks (LAN), wide area networks (WAN), personal area networks (PAN), cellular or data networks, and/or the Internet.

Various devices and subsystems may be connected to the network 110. For example, one or more medical scanners may be connected, such as MRI scanners 120. The MRI scanners 120 may be used to acquire MRI images from patients, and may share the acquired images with other devices on the network 110. The network 110 may also be coupled to one or more CT scanners 122. The CT scanners 122 may also be used to acquire images and, like the MRI scanner 120, may then store those images and/or share those images with other devices via the network 110. Any other scanner or device capable of inputting or generating information could be included, including ultrasound, angiography, nuclear medicine, radiography, endoscopy, pathology, dermatology, etc.

Also connected to the network 110 may be a Picture Archiving and Communications System (PACS) 136 and PACS workstation 138. The PACS 136 is typically used for the storage, retrieval, distribution and presentation of images (such as those created and/or generated by the MRI scanner 120 and CT Scanner 122). The medical images may be stored in an independent format, an open source format, or some other proprietary format. A common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 110 may also be connected to a Radiology Information System (RIS) 140. The radiology information system 140 is typically a computerized data storage system that is used by radiology departments to store, manipulate and distribute patient radiological information such as Radiology Reports.

Also attached to the network 110 may be an Electronic Medical Record (EMR) system 142. The EMR system 142 may be configured to store and make accessible to a plurality of medical practitioners computerized medical records. Also attached to the network 110 may be a Laboratory Information System 144. Laboratory Information System 144 is typically a system which stores information created or generated by clinical laboratories. Also attached to the network 110 may be a Digital Pathology System 146 used to digitally manage and store information related to medical pathology.

Also attached to the network 110 may be a Computer Aided Diagnosis System (CAD) 148 used to analyze images. In one embodiment, the CAD 148 functionality may reside in a computing device separate from Information Display Computing Device 150 while in another embodiment the CAD 148 functionality may reside within Information Display Computing Device 150.

Also attached to the network 110 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from Information Display Computing Device 150 while in another embodiment the 3D Processing functionality may reside within Information Display Computing Device 150.

In other embodiments, other computing devices that store, provide, acquire, and/or otherwise manipulate medical data may also be coupled to the network 110 and may be in communication with one or more of the devices illustrated in FIG. 9, such as with the Information Display Computing Device 150.

As will be discussed herein, Computing Device 150 may be configured to interface with various networked computing devices in order to communicate medical information that is stored among the various systems present in the network. In other embodiments, Information Display Computing Device 150 may be used to display non-medical information.

Depending on the embodiment, the other devices illustrated in FIG. 9 may include some or all of the same components discussed above with reference to the Information Display Computer Device 150.

SUMMARY

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of customizing display of items, the method comprising:
   monitoring selection of items for display on one or more display devices of a computing system, wherein the items include at least one of documents, images, forms, or dialogs associated with a patient;
   monitoring changes in one or more of a size or position of items displayed on the one or more display devices; and
   in response to detecting a change in one or more of a size or position of a particular item of the items displayed on the computing device,
      determining a category of the changed item from a group of categories including one or more of documents, images, forms, or dialogs;
      creating or updating category information associated with the determined category, the category information including:
         a user of the computing system;
         one or more display characteristics of the one or more display devices on which the particular item is displayed; and
         at least one of size or position of the particular item after the detected change;
      storing the category information such that it is usable by at least one of the computing system or other computer systems in order to automatically adjust at least one of a size or position of other items selected for display by the user that are also within the determined category, such that a size and position of the other items match the size and position of the particular item.

2. The method of claim 1, wherein the category information is further associated with a medical exam such that subsequent selection of the medical exam results in display of the particular item at the size and position stored in the category information.

3. The method of claim 1, wherein the category information further comprises associations between one or more other items and respective sizes or positions, categories, users, and display characteristics.

4. The method of claim 3, wherein the category information further comprises an arrangement of multiple items of an exam such that subsequent selection of the exam results in display of the multiple items at the respective sizes and positions stored in the associated category information.

5. The method of claim 4, wherein the category information is stored with the exam.

6. The method of claim 5, wherein the category information is stored on a network accessible device so that the category information is accessible to determine at least one of the arrangement or size and position of items of the exam selected on other computing systems.

7. The method of claim 1, wherein the categories comprise at least one of types of documents, types of images, types of forms, or types of dialogs.

8. The method of claim 1, wherein the one or more display characteristics include one or more of a resolution of the one or more displays, an aspect ratio of the one or more displays, and whether the one or more displays are color or black and white.

9. The method of claim 1, wherein the category information further comprises associations between a second at least one of size or position, the same determined category, the same determined user, and a second one or more display characteristics.

10. The method of claim 9, further comprising:
    in response to selection of a second particular item for display on a display device having about the second one or more display characteristics, adjusting at least one of a size or position of second particular item to the size and position associated with the second one or more characteristics.

11. The method of claim 10, wherein the display device is determined to have about second one or more display characteristics if a resolution of the display device is less than 5% different than a resolution included in the second one or more display characteristics.

12. The method of claim 1, further comprising:
    providing a user interface on a first of the one or more display devices for selection of the particular item for display on a second of the one or more display devices having the determined one or more display characteristics such that the particular item is selected by the user interface on the first of the one or more display devices and displayed on the second of the one or more display devices.

13. The method of claim 1, wherein the method further comprises:
    determining whether a second display device is within a range of acceptable characteristics for displaying the particular item according to the item information, and
    in response to user selection of the particular item for display on the second display device, only use the at least one of size or position of the particular item if the second display device is within the range of acceptable characteristics.

14. The method of claim 1, wherein the item information further comprises information indicating an arrangement of multiple categories of items displayed on the one or more display devices.

15. The method of claim 14, further comprising:
    in response to selection of a plurality of items for display, determining whether the multiple categories of items are included in the plurality of items and, in response to determining that the multiple categories of items are included in the plurality of items, determining at least one of a size or position of the plurality of items according to the item information associated with the respective categories.

16. The method of claim 14, wherein the item information indicates respective display devices on which items of respective categories are displayed.

17. The method of claim 1, wherein at least one of the computing system or other computer systems automatically adjust at least one of a size or position of other items selected for display that are also within the determined category in response to determining that at least one of a resolution of the computing system or other computer system is about the determined resolution.

18. The method of claim 1, wherein the other items selected for display by the user that are also within the determined category are of a second patient.

\* \* \* \* \*